(12) United States Patent
Forte

(10) Patent No.: US 6,228,851 B1
(45) Date of Patent: May 8, 2001

(54) PROCESS FOR THE PURIFICATION OF 11β-21-DIHYDROXY-2'-METHYL-5'βH-PREGNA-1,4-DIENO[17,16-D]OXAZOLE-3,20-DIONE

(75) Inventor: Luigi Forte, Brindisi (IT)

(73) Assignee: Gruppo Lepetit S.p.A., Milan (IT)

( * ) Notice: Subject to any disclaimer, the term of this patent is extended or adjusted under 35 U.S.C. 154(b) by 0 days.

(21) Appl. No.: 09/117,882

(22) PCT Filed: Dec. 4, 1996

(86) PCT No.: PCT/EP96/05392

§ 371 Date: Aug. 7, 1998

§ 102(e) Date: Aug. 7, 1998

(87) PCT Pub. No.: WO97/30068

PCT Pub. Date: Aug. 21, 1997

(30) Foreign Application Priority Data

Feb. 16, 1996 (EP) .................................. 96102325

(51) Int. Cl.[7] ............... A61K 31/58; C07J 71/00
(52) U.S. Cl. ................................. 514/176; 540/56
(58) Field of Search ........................ 514/176, 56

(56) References Cited

PUBLICATIONS

A. Santos–Montes, J. of Chromatography B : Biochemical Applications, vol. 652, No. 1, Jan. 14, 1994, pp 83–89.

E. Martinelli et al, Drug Metabolism and Disposition, vol. 7, No. 5 (9–10/79) pp 335–339, 1979.

A. Assandri et al, Xenobiotica, vol. 13, No. 3, Mar. 1983, pp 185–196.

A. Santos–Montes et al, J. of Chromatography B : Biochemical Applications, vol. 657, No. 1, Jul. 1, 1994, pp 248–253.

*Primary Examiner*—Mukund J. Shah
*Assistant Examiner*—Brenda Coleman
(74) *Attorney, Agent, or Firm*—Balaram Gupta

(57) ABSTRACT

Process for preparing the compound 11β-21-dihydroxy-2'-methyl-5'βH-pregna-1,4-dieno[17,16-d]oxazoline-3,20-dione of formula (I):

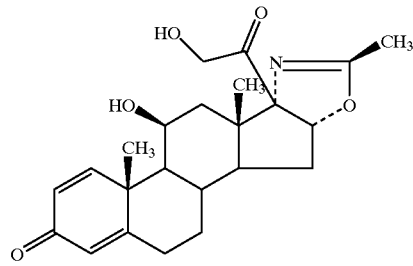

which comprises adsorbing said compound, contained into an aqueous solution resulting from fermentation broths or process streams, on an adsorbent polymeric resin having a styrenic or acrylic matrix and subsequently desorbing the said compound by eluting the resin with suitable mixture of water with a water-miscible organic solvent.

15 Claims, No Drawings

PROCESS FOR THE PURIFICATION OF 11β-21-DIHYDROXY-2'-METHYL-5'βH-PREGNA-1,4-DIENO[17,16-D]OXAZOLE-3,20-DIONE

This application is a national stage entry under 35 U.S.C. § 371 of PCT/EP96/05392, filed Apr. 12, 1996.

The present invention refers to a new process for the purification of the compound 11β-21-dihydroxy-2'-methyl-5'βH-pregna-1,4-dieno[17,16-d-]oxazoline-3,20-dione of formula I;

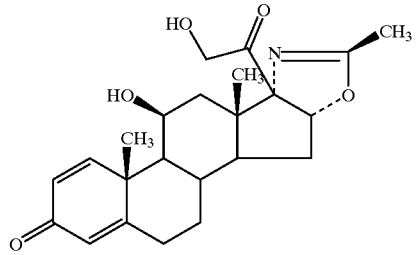

The above compound is related to deflazacort (INN—International Nonproprietary Name), in that the acetate moiety on the C-21 of deflazacort is substituted by a hydroxy moiety.

Deflazacort is a compound employed in therapy since some years as a calcium-sparing gluco-corticoid agent.

These compounds belong to the more general class of pregneno-oxazolines, for which anti-inflammatory, glucocorticoid and hormone-like pharmaceological activities are reported. Examples of compounds of the above class are disclosed in U.S. Pat. No. 3,413,286 and U.S. Pat. No. 4,440,764.

The preparation of the compound of formula I is disclosed in EP-B-322630, wherein said compound is referred to as 11β-21-dihydroxy-2'-methyl-5'βH-pregna-1,4-dieno[17,16-d]oxazoline-3,20-dione.

According to the fermentation process disclosed in the above cited EP-B-322630, 2'-methyl-4-pregnen-21-ol-[17a,16a-d]oxazolinyl-3,20-dione or 2'-methyl-4-pregnen-21-acetyloxy-[17a,16a-d]oxazolinyl-3,20-dione is contacted with a sequentially growing mixed culture of a Curvularia strain and an Arthrobacter strain. More in particular, according to a preferred embodiment, the above compound is added to a growing culture of C. lunata NRRL 2380 in a suitable fermentation medium after 12–24 hours from inoculum, and, after 48–72 hours from inoculum, a growing culture of A. simplex ATCC 6946 of 18–36 hours is added to the mixture and further cultivated for 40–55 hours; the fermentation is carried out under submerged conditions, temperature is kept between 27° C. and 32° C. and pH between 6 and 8; the fermentation product of formula I is then recovered by extracting the fermentation broth with an organic solvent (e.g. chloroform), concentrating the organic extracts and precipitating the compound by adding a non-solvent (e.g. petroleum ether).

As the concentration of the compound of formula I in the fermentation broth is very low, high amounts of organic solvent are necessary for completely extracting the compound. The use of high amounts of organic solvents, in particular halogenated solvents, may give rise to some problems, with respect to the safety, industrial hygiene and environment protection.

It has now been found that the compound of formula I can be conveniently recovered from an aqueous solution resulting from fermentation broths or process streams, by adsorbing the compound contained in said aqueous solution on an adsorbent polymeric resin having a styrenic or acrylic matrix and subsequently desorbing the said compound by eluting the resin with a suitable mixture of water with a water-miscible organic solvent.

Typical aqueous solutions containing the compound of formula I accompained by undesired products are the filtered fermentation broths from the suitable mycelia, optionally together with the aqueous washings of said mycelia, or partially purified process streams. Examples of the undesired accompanying products are colored impurities, side-products, unhexausted starting materials, salts and water soluble components of the fermentation media.

In particular, the purification process of the present invention may conveniently be applied for recovering the compound of formula I from the filtered fermentation broth obtained from the fermentation process disclosed in EP-B-322630.

Suitable resins for the present purification process will have an average particle size of about 20–50 mesh and the following average physical characteristics:
Porosity volume: about 30%–75%;
Surface Area: about 140–800 m$^2$/g;
Skeletal Density: about 1.06–1.10 g/ml (styrenic resin) about 1.20–1.26 g ml (acrylic resins);
Average pore diameter: about 20–100 Å.

Examples of adsorbent styrenic based polymeric resins suitable for the above recovering process are the commercially available resins such as Kastel® S/112 (Dow Chemical), Amberlite® XAD/2, XAD/4 or XAD/16 (Rohm & Haas), or the like. Examples of adsorbent acrylic based polymeric resins suitable for the above recovering process are the commercially available resins such as Kastel® S/221 or S/223 (Dow Chemical), Amberlite® XAD/7 or XAD/8 (Rohm & Haas), and the like.

In general for the process of the present invention, the acrylic based polymeric resins are preferably employed, particularly preferred being those having a particle size of about 20–50 mesh and the following average physical characteristics:
Porosity volume: about 30%–60%
Surface Area: about 350–550 m$^2$/g;
Skeletal Density: about 1.24–1.25 g/ml;
Average pore Diameter: about 20–80 Å.

Examples of adsorbent acrylic based polymeric resins with the above characteristics which may be suitably employed are the previously mentioned Kastel® S/221 and Amberlite® XAD/7.

Particularly preferred for the present purification process is an acrylic based polymeric resins having a particle size of about 20–50 mesh and the following average physical characteristics:
Porosity volume: about 30%–60%
Surface Area: about 350–550 m$^2$/g;
Skeletal Density: about 1.25 g/ml;
Average pore Diameter: about 20–40 Å.

For instance, the commercially available resin Kastel® S/221 may suitably be employed.

Suitable eluting mixtures are mixtures from 0% to 80% of water with a water miscible organic solvent such as lower ketones (e.g. acetone, ethylmethylketone); lower alcohols (e.g. methanol, ethanol, propanol, butanol); and the like.

Preferably, mixtures from 10% to 50% of water with one of the above organic solvents are employed, particularly preferred being a mixture containing about 30% of water Acetone is the preferred solvent.

When the process of the present invention is employed for the purification of the compound of formula I obtained according to the fermentation process as described in EP-B-322630, the following general procedure may conveniently be applied.

When the said fermentation process is completed, the fermentation mass is first filtered according to the known techniques. The mycelial cake is repeatedly washed with water and the washings are then combined with the filtered broth. Alternatively, the mycelium can be washed with an organic solvent selected from those previously listed, in order to recover the activity contained therein; in this case, the washings are combined with the filtered broth only after having removed the solvent, e.g. by stripping under vacuum.

The filtered broth combined with the washings is then applied on the top of a column containing the adsorbing resin; in general, the eluted solution contains only traces of product. The resin is then washed with water for eliminating salts and other water-soluble impurities (as above, also this washing water will generally contain only traces of the product).

The compound of formula I is then desorbed from the resin, by eluting with a mixture of water and an organic solvent as above defined, preferably a mixture 30/70 water/acetone. The eluate is concentrated and the product is recovered by filtration. With this procedure the major amount of product is recovered from the filtered broth; as a general indication, more than 90% of the total amount of the desired compound initially applied on the column is recovered with this first elution.

The remaining amount can be recovered by repeating the above procedure after having combined the mother liquors from the first elution and the washings with water. The total recovery yield is about 96%.

For better illustrating the invention, the following examples are given.

Example 1 Sequential Growth of C. lunata and A. simplex

I) Slant Media
  Sabouraud medium (for C. lunata)
  Antibiotic Agar No. 1 (for A. simplex)
II) Vegetative and pre-culture media
  a) for C. lunata
  Soybean meal 13 g/l
  $KH_2PO_4$ 5 g/l
  Dextrose 10 g/l
  Peptone 5 g/l
  pH adjusted to 6.5–7.5 before autoclaving;
  b) for A. simplex
  Dextrose 1.0 g/l
  Soybean meal 5.0 g/l
  Peptone 5.0 g/l
  Basamin Busch 3.0 g/l
  $KH_2PO_4$ 5.0 g/l
  NaCl 5.0 g/l
  Silicone 0.1 ml/l
  pH adjusted to 6.5–7.5 before autoclaving.
III) Fermentation media
  A fermentation medium having the same composition of the pre-culture medium of C. lunata reported above.
IV) Fermentation procedure
  The slants are used to separately inoculate 500 ml flasks which are cultured at about 28° C. for about 12–24 h (C. lunata) or 18–36 h. (A. simplex) in the presence of 100 ml of the vegetative media indicated above. These inocula are used in the procedure described below:

Aliquots (about 1 to 5%) of the culture of C. lunata obtained above are transferred in a 8 liter fermentor containing the above reported fermentation medium and cultivated for about 24 h at 29–32° C.

Then 4 g of 2'-methyl-4-pregnen-21-ol-[17a,16a-d]-oxazolinyl-3,20-dione are added and the fermentation is continued until about 36–72 h from the inoculum.

Afterwards, the 18–36 h culture of A. simplex is added thereto and the fermentation is continued for further 40–55 h.

The reaction course is monitored as known in the art by TLC or preferably HPLC by following the disappearance of the starting material and/or appearance of the final product. As a further control, the appearance disappearance of intermediates can also be followed. HPLC conversion yield: 70–75%.

Example 2 Recovery of the Compound of Formula I

After 40–55 h from the addition of A. simplex, the transformation can be generally considered as completed and the fermentation mass can be worked up to isolated the desired compound of formula I.

The pH of the fermentation mass is adjusted at about 3–4 with $H_2SO_4$ and the mixture is separated by filtration using filter aid; the filtered mycelium is then repeatedly washed with acidified water (3<pH<4). The filtered broth and the washings are combined, obtaining 11 l of a mixture containing the compound of formula I, with a title of 270 ppm (determined by HPLC on silica gel; Column Spherisorb 3 $\mu$m, 100×4, 6 mm; flow rate 1.3 ml/min, mobile phase 0.0025M $NaH_2PP_4$:$CH_3CN$ 7:3, UV Detector at 254 nm). The above mixture is then applied at room temperature on the top of a chromatographic column (6×11 cm) containing about 300 ml of an aqueous-swollen acrylic based polymeric resins (Kastel® S/221, Dow Chemical), at a flow rate of about 300 ml/h. The eluted broth (mother liquors), which contains less than 2 ppm of activity, is collected separately.

The resin is then washed with 600 ml of demineralized water for removing salts and other water-solubile impurities. Also in this case the eluate (washings), which contains less than 2 ppm of activity, is collected separately.

The product is then desorbed from the resin by eluting with a mixture 70/30 of acetone/water at a flow rate of about 150 ml/h, collecting about 200 ml of eluate.

The eluate is concentrated under vacuum at a volume of about 100 ml, while product precipitates.

The suspension is cooled to about 5° C. and after 2 hours the precipitate is collected by filtration and washed with cold water. After drying under vacuum at 50° C., 2.8 g of the compound of formula I are obtained (title 98%).

Mother liquors and washings are combined and after diluting with water (about 1–2 volume with respect to the volume of mother liquors) are applied on the top of a column (2×13 cm) containing 40 ml of the above swollen resin at a flow rate of about 40 ml/h.

After washing the resin with 80 ml of water, the product is desorbed by eluting with a mixture 70/30 of acetone/water at a flow rate of about 20 ml/h. Upon concentration under vacuum, cooling, filtration, washing with cold water and drying, further 0.14 g of the compound of formula I are obtained.

The total recovery yield from the fermentation mixture is typically about 96%.

By repeating the procedure outlined in Example 1 and 2, but using 2'-methyl-4-pregnen-21-acetyloxy-[17a,16a-d]-oxazolinyl-3,20-dione instead of 2'-methyl-4-pregnen-21-ol-[17a,16a-d]-oxazolinyl-3,20-dione, the compound of formula I is obtained substantially with the same yields.

What is claimed is:

1. A process for the purification of the compound 11β-21-dihydroxy-2'-methyl-5'βH-pregna-1,4-dieno[17,16-d]-oxazoline-3,20-dione of formula I;

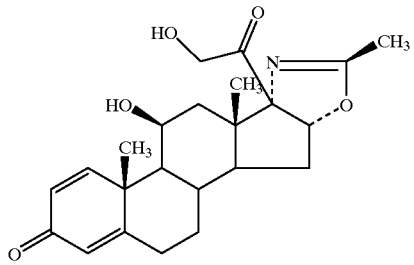

which comprises adsorbing said compound, contained in an aqueous solution resulting from fermentation broths or process streams, on an aqueous swollen adsorbent polymeric resin having a styrenic or acrylic matrix and subsequently desorbing the said compound by eluting the resin with a suitable mixture of water and a water-miscible organic solvent.

2. The process according to claim 1, wherein the fermentation broth containing the compound of formula I is that obtained from the fermentation process for obtaining said compound, which comprises contacting 2'-methyl-4-pregnen-21-ol-[17a,16a-d-]oxazolinyl-3,20-dione or 2'-methyl-4-pregnen-21-acetyloxy-[17a,16a-d-]oxazolinyl-3,20-dioine with a sequentially growing mixed culture of a Curvularia strain and a Arthrobacter strain.

3. The process according to claim 1 wherein the eluting mixture contains about 30% water.

4. The process according to claim 1 or 2 wherein:
a) the fermentation broth is first filtered, the mycelial cake is repeatedly washed with water and the washings are then combined with the filtered broth;
b) the filtered broth combined with the washings is then applied on the top of a column containing the aqueous-swollen adsorbing resin;
b') the resin is washed with water;
c) the compound of formula I is desorbed from the resin by eluting with a mixture 30/70 water/acetone;
d) the eluate is concentrated and the compound of formula I is recovered by filtration.

5. The process according to claim 4 wherein the purification procedure is repeated on the combined mother liquors and the washings obtained from the elution according to steps b and b'.

6. The process according to claim 2 wherein the eluting mixture contains about 30% water.

7. The process according to claim 2 wherein the aqueous swollen adsorbent polymeric resin is a polymeric resin having a styrenic or acrylic matrix having a particle size of about 20–50 mesh and with the following average physical characteristics:
Porosity volume: about 30%–75%;
Surface Area: about 140–800 $m^2/g$;
Skeletal Density: about 1.06–1.10 g/ml for styrenic resins, About 1.20–1.26 g/ml for acrylic resins;
Average pore Diameter: about 20–100 Å.

8. The process according to claim 2 wherein the aqueous swollen adsorbent polymeric resin is an acrylic based polymeric resin having a particle size of about 20–50 mesh and the following average physical characteristics:
Porosity volume: about 30%–60%;
Surface Area: about 350–550 $m^2/g$;
Skeletal Density: about 1.24–1.25 g/ml;
Average pore Diameter: about 20–80 Å.

9. The process according to claim 2 wherein the aqueous swollen adsorbent polymeric resin is an acrylic based polymeric resin having a particle size of about 20–50 mesh and the following average physical characteristics:
Porosity volume: about 30%–60%;
Surface Area: about 350–550 $m^2/g$;
Skeletal Density: about 1.25 g/ml;
Average pore Diameter: about 20–40 Å.

10. The process according to claim 3, 1 or 5 wherein the adsorbent polymeric resin is a polymeric resin having a styrenic or acrylic matrix having a particle size of about 20–50 mesh and with the following average physical characteristics:
Porosity volume: about 30%–75%
Surface Area: about 140–800 $m^2/g$;
Skeletal Density: about 1.06–1.10 g/ml for styrenic resins, about 1.20–1.26 g/ml for acrylic resins;
Average pore Diameter: about 20–100 Å.

11. The process according to claim 3, 1 or 6 wherein the adsorbent polymeric resin is an acrylic based polymeric resin having a particle size of about 20–50 mesh and the following average physical characteristics:
Porosity volume: about 30%–60%;
Surface Area: about 350–550 $m^2/g$;
Skeletal Density: about 1.24–1.25 g/ml;
Average pore Diameter: about 20–80 Å.

12. The process according to claim 3, 1 or 6 wherein the adsorbent polymeric resin is an acrylic based polymeric resin having a particle size of about 20–50 mesh and the following average physical characteristics:
Porosity volume: about 30%–60%
Surface Area: about 350–550 $m^2/g$;
Skeletal Density: about 1.25 g/ml;
Average pore Diameter: about 20–40 Å.

13. The process according to claim 2, 3, 1 or 6 wherein the water miscible organic solvent is a lower ketone or a lower alcohol.

14. The process according to claim 2, 3, 1 or 6 wherein the organic solvent is acetone.

15. The process according to claim 2, 3, 1 or 6 wherein the eluting mixture is a mixture 30/70 water/acetone.

* * * * *